US011446346B2

(12) United States Patent
Bharate et al.

(10) Patent No.: US 11,446,346 B2
(45) Date of Patent: Sep. 20, 2022

(54) **GASTRORETENTIVE SUSTAINED RELEASE FORMULATIONS OF *BERGENIA CILIATA***

(71) Applicant: COUNCIL OF SCIENTIFIC & INDUSTRIAL RESEARCH, New Delhi (IN)

(72) Inventors: Sonali Sandip Bharate, Jammu (IN); Rohit Singh, Jammu (IN); Mehak Gupta, Jammu (IN); Bikarma Singh, Jammu (IN); Anil Kumar Katare, Jammu (IN); Ajay Kumar, Jammu (IN); Sandip Bibishan Bharate, Jammu (IN); Ram Vishwakarma, Jammu (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/755,919

(22) PCT Filed: Sep. 11, 2018

(86) PCT No.: PCT/IN2018/050588
§ 371 (c)(1),
(2) Date: Apr. 14, 2020

(87) PCT Pub. No.: WO2019/077620
PCT Pub. Date: Apr. 25, 2019

(65) Prior Publication Data
US 2020/0316150 A1 Oct. 8, 2020

(30) Foreign Application Priority Data

Oct. 16, 2017 (IN) .............................. 201711036683

(51) Int. Cl.
*A61K 36/00* (2006.01)
*A61K 36/185* (2006.01)
*A61K 9/20* (2006.01)
*A61K 9/48* (2006.01)
*A61K 31/7034* (2006.01)

(52) U.S. Cl.
CPC .......... *A61K 36/185* (2013.01); *A61K 9/2054* (2013.01); *A61K 9/4866* (2013.01); *A61K 31/7034* (2013.01)

(58) Field of Classification Search
CPC ...................................................... A61K 36/00
USPC ........................................................ 424/725
See application file for complete search history.

(56) References Cited

U.S. PATENT DOCUMENTS

2005/0158380 A1* 7/2005 Chawla ................ A61K 9/2027
424/465

FOREIGN PATENT DOCUMENTS

| CN | 1660078 A | * | 8/2005 |
| CN | 1660078 A |   | 8/2005 |
| CN | 101797253 A | * | 8/2010 |
| CN | 1010797253 A |   | 8/2010 |
| WO | 2014188440 A1 |   | 11/2014 |

OTHER PUBLICATIONS

Gehlot et al., "Some Pharmacological Studies on Ethanolic Extract of Roots of Bergenia Ligulata", Indian J. Pharmacol 1976, 8, 92.
Afran et al., "Molecular simulations of bergenin as a new urease inhibitor", Med Chem Res, vol. 21, pp. 2454-2457, 2012.
De Oliveria et al., "Antinociceptive Properties of Bergenin", Journal of Natural Products, vol. 74, pp. 2062-2068, 2011.
Goole et al., "Development and evaluation of new multi8ple-unit levodopa sustained-release floating dosage forms", International Journal of Pharmaceutics, vol. 334, pp. 35-41, 2007.
Hay et al., "Bergenin, a C-Glycopyranosyl Derivative of 4-O-Methylgallic", Analyt. Chem., vol. 26, No. 920, pp. 2231-2238, 1954.
Jain et al., "Pyrano-isochromanones as IL-6 Inhibitors: Synthesis, in Vitro and in Vivo Antiarthritic Activity", Journal of Medicinal Chemistry, vol. 57, pp. 7085-7097, 2014.
Klausner et al., "Expandable gastroretentive dosage forms", Journal of Controlled Release, vol. 90, pp. 143-162, 2003.
Liang et al., "In vivo and in vitro antimalarial activity of bergenin", Biomedical Reports 2, pp. 260-264, 2014.
Lim et al., "Hepatoprotective effects of bergenin, a major constituent of Mallotus japonicus, on carbon tetrachloride-intoxicated rats", Journal of Ethnopharmacology, vol. 72, pp. 469-474, 2000.
Lopes et al., "Overviewon gastroretentive drug delivery systems for improving drug bioavailability", International Journal of Pharmaceutics, vol. 510, pp. 144-158, 2016.

(Continued)

*Primary Examiner* — Michael V Meller
(74) *Attorney, Agent, or Firm* — Dinsmore & Shohl, LLP

(57) ABSTRACT

The present invention is related to a novel gastroretentive swellable oral dosage form for sustained or delayed release of bergenin, a active constituent of *Bergenia ciliata* extract/fraction and a process for preparing the same wherein the extract is wet-granulated using excipients i.e. biodegradable polymers and/or non-biodegradable polymers alone or in combination, and the said granules are either filled into a capsule or compressed into a tablet. The said formulation comprising a granulated extract of bergenin-rich *Bergenia ciliata* with polymers has resulted in a sustained release of extract in the stomach over a period of 16-24 hrs. The said formulations are useful for the treatment of inflammatory diseases.

7 Claims, 6 Drawing Sheets

(56) References Cited

OTHER PUBLICATIONS

Nazir et al., "Immunomodulatory effect of bergenin and norbergenin against adjuvant-induced arthritis-A flow cytometric study", Journal of Ethnopharmacology, vol. 112, pp. 401-405, 2007.

Park, K., "Enzyme-digestible swelling hydrogels as platforms for long-term oral drug delivery: synthesis and characterization", Biomaterials, vol. 9, pp. 435-441, Sep. 1988.

Pu et al., "Bergenin in the Antiarrhythmic Principle of Fluggea virosa", Planta Med, vol. 68, pp. 372-374, 2002.

Rouge et al., "Comparative pharmacokinetic study of a floating multiple-unit capsule, a high-density multiple-unit capsule and an immediate-release tablet containing 25 mg atenolol", Pharmaceutica Acta Helvetiae, vol. 73, pp. 81-87, 1998.

Santus et al., "An in vitro—in vivo investigation of oral bioadhesive controlled release furosemide formulations", European Journal of Pharmaceutics and Biopharmaceutics, vol. 44, pp. 39-52, 1997.

Sharma et al., "Low density multiparticulate system for pulsatile release of meloxicam", Internal Journal of Pharmaceutics, vol. 313, pp. 150-158, 2006.

Singh et al., "Synthesis, pH dependent, plasma and enzymatic stability of bergenin prodrugs for potential use against rheumatoid arthritis", Bioorganic & Medicinal Chemistry, vol. 25, pp. 5513-5521, 2017.

Streubel, et al., "Multiple unit gastroretentive drug delivery systems: a new preparation method for low density microparticles", J. Microencapsulation, vol. 20, No. 3, pp. 329-347, 2003.

Takahashi et al., "Synthesis and Neuoprotective Activity of Bergenin Derivatives with Antioxidant Activity", Bioorganic & Medicinal Chemistry, vol. 11, pp. 1781-1788, 2003.

Zhou et al., "Physicochemical properties of bergenin", Pharmazie, vol. 63, No. 5, pp. 366-371, 2008.

He et al., Formulation and evaluation of novel coated floating tablets of bergenin and cetrizine dihydrochloride for gastric delivery. Drug Development and Industrial Pharmacy, vol. 38, No. 10, pp. 1280-1288 Oct. 1, 2012.

Search Report and Written Opinion pertaining to PCT/IN2018/050588 dated Nov. 27, 2018.

Fujimori et al., "Preparation of a magnetically-responsive tablet and confirmation of its gastric residence in beagle dogs", Abstract only, S.T.P. Pharma Sciences, vol. 4, Issue 6, 1994, pp. 425-430.

* cited by examiner

BCHA-29　　　　　　　BCHA-29　　　　　　　　　BCE-8
Zero min　　　End of 24 h: intact, swellable　　End of 24 h: intact, swellable

Swelling index (SI) = $\dfrac{W_t - W_0}{W_0} \times 100$

Where, S.I. = swelling index (% weight gain by formulation)
$W_t$ = weight of capsule at time t
$W_0$ = weight of capsule before immersion

| Formulation code | Swelling index (%) |
|---|---|
| BCHA-18 | 489 |
| BCHA-28 | 534 |
| BCHA-29 | 361 |
| BCE-8 | 358.5 |

GASTRORETENTIVE SUSTAINED RELEASE FORMULATIONS OF BERGENIA CILIATA

CROSS-REFERENCES TO RELATED APPLICATIONS

This application is a national-stage application under 35 U.S.C. § 371 of International Application No. PCT/IN2018/050588, filed Sep. 11, 2018, which International Application claims benefit of priority to Indian Patent Application No. 201711036683, filed Oct. 16, 2017.

FIELD OF THE INVENTION

The present invention relates to the novel gastroretentive swellable oral formulations for sustained or delayed release of bergenin-rich *Bergenia ciliata* extract/fraction and a process for preparing the same. In particular, the present invention relates to novel formulations which gets retained in the stomach, and thereby avoids intestinal degradation of the active constituent 'bergenin', resulting in sustained release of active constituent in stomach over a period of 16-24 hrs. The said formulations are useful for the treatment of inflammatory diseases.

BACKGROUND OF THE INVENTION

Gastroretentive drug delivery (GRDD) is an approach to prolong gastric residence time, thereby targeting site-specific drug release in the upper gastrointestinal tract (GIT) i.e. stomach. Such delivery systems are particularly useful for drugs which are unstable in intestinal environment. After oral administration, such drug delivery would be retained in the stomach and releases the drug in a controlled manner, so that the drug could be supplied continuously to its absorption sites in the GIT. Several GRDD formulations are also commercially available in the market, for example, Madopar HBS® (active constituent: Levodopa), Valrelease® (active constituent: diazepam), Topalkan® (active constituent: alginic acid), and Almagate Flotcoat (active constituent: levofloxacin).

Over the last few decades, several GRDD approaches were designed and developed, including: high density (sinking) systems that is retained in the bottom of the stomach (image 'c' from the Schematic diagram shown below) (Rouge N et al., *Pharm Acta Helbetiae* 1998, 73, 81), low density (floating) systems that causes buoyancy in gastric fluid (image 'd') (Streubel A et al, *J Microencapsul* 2003, 20, 329; Goole J et al, *Int J Pharm* 2007, 334, 351; Sharma S and Pawar A. *Int J Pharm* 2006, 313, 150), mucoadhesive systems that causes bioadhesion to stomach mucosa (image 'a') (Santus G et al, *Eur J Pharm Biopharm* 1997, 44, 39), unfoldable, extendible, or swellable systems which limits emptying of the dosage forms through the pyloric sphincter of stomach (image 'b') (Klausner E A et al, *J Control Release* 2003, 90, 143), and other systems such as superporous hydrogel systems (Park K, *Biomaterials* 1988, 9, 435), magnetic systems (Fujimori J et al, *STP Pharma Sci* 1994, 4, 425) (Lopez C M et al, *Int J Pharm.* 2016, 510, 144) etc. The density controlled drug delivery system is further of two types viz. effervescent system and non-effervescent system. In effervescent system, either gas generating or volatile liquid containing systems are used, in order to make the formulation floatable in gastric fluid. In gas generating system, carbonates or bicarbonates are used (e.g. sodium bicarbonate) which react with gastric acid to produce carbon dioxide which reduces the density of formulation, making it buoyance or float on the media. However, non-effervescent density controlled system consists of gel-forming, highly swellable cellulosic hydrocolloids (e.g. HPMC, HEC) or matrix forming polymers (e.g. sodium alginate, ethyl cellulose). After oral administration, this dosage form swells in contact with gastric fluids. The air entrapped within the swollen matrix imparts buoyancy to the dosage form making it either float or sink in the medium. The so formed swollen gel-like structure acts as a reservoir and allows sustained release of drug through the gelatinous mass. The pictorial representation of floating drug delivery systems is shown in FIG. 6.

*Bergenia ciliata* (also known as *Saxifraga ligulata*; Family: Saxifragaceae) is one of the most important medicinal herbs in India, which widely occurs in temperate Himalayas from Kashmir to Bhutan and in Khasi hills at 1500 m altitude. The rhizomes of *Bergenia ciliata* have been used for centuries in the Ayurvedic medicine to treat kidney and bladder stones, abnormal leucorrhea, piles, and pulmonary affections, and its decoction is used for the treatment of various pain conditions. The alcoholic extract is reported to have anti-inflammatory, analgesic and diuretic properties (Gehlot, N. K. et al., *Indian J. Pharmacol.* 1976, 8, 92). The major chemical constituent of the plant bergenin (Hay, J. E. et al., *J. Chem. Soc.* 1958, 2231) is also reported to possess several pharmacological activities including hepatoprotective (Lim, H. K. et al., *J. Ethnopharmacol.* 2000, 72, 469), antiarrhythmic (Pu, H. L. et al., *Planta Med.* 2002, 68, 372-374), antiulcer (Arfan, M. et al., *Med Chem. Res.* 2012, 21, 2454), neuroprotective/antioxidant (Takahashi, H. et al., *Bioorg. Med Chem.* 2003, 11, 1781), anti-inflammatory (de Oliveira, C. M. et al., *J. Nat. Prod.* 2011, 74, 2062-2068; Jain S K et al, *J. Med. Chem.* 2014, 57, 7085; WO2014188440), immunomodulatory (Nazir, N. et al., *J. Ethnopharmacol.* 2007, 112, 401) and antimalarial activities (Liang, J. et al., *Biomed Rep.* 2014, 2, 260).

Bergenin, a major bioactive constituent of *Bergenia ciliata*, despite of its interesting biological activities, it has certain stability concerns. Study indicated that bergenin gets degraded at intestinal pH (pH 6.8 and above), however it is stable at acidic pH of stomach (pH 1.2) (Singh, R. et al., *Bioorg. Med Chem.* 2017, dx.doi.org/10.1016/j.bmc.2017.08.011; Zhou, D. et al., *Pharmazie* 2008, 63, 366). Zhou et al reported that the degradation half life of bergenin at pH 7 and pH 8 is 14.4 and 2.9 hrs (Zhou D. et al., *Pharmazie* 2008, 63, 366). Furthermore, in pharmacokinetic study in rats, the plasma half-life of bergenin is low ($t_{1/2}$=1-2 hrs). Also the conventional formulations of herbal extracts have difficulty in filling into capsules because of their characteristic strong hygroscopicity. Therefore in view of the above, there is a need to develop formulation of *Bergenia ciliata* to overcome the existing drawbacks.

Thus, a gastro retentive sustained release formulation would be an ideal drug delivery system for effective delivery of this bioactive constituent from the *Bergenia ciliata* extract.

OBJECTIVES OF THE INVENTION

The main objective of this invention is to provide novel gastroretentive sustained release formulations of *Bergenia ciliata* extract/fraction capable of avoiding the intestinal degradation of active ingredient via retaining the formulation in gastric environment.

Also another object of the present invention is to provide an oral sustained release formulation for delayed release of the active ingredient over the period of up 16 to 24 hrs.

It is also an objective of this invention to provide novel gastroretentive sustained release formulations containing elevated concentrations of bergenin obtained by means of the process.

It is another objective of this invention to provide the use and method of application of this formulation for treatment of inflammatory diseases involving elevated levels of pro-inflammatory cytokines.

SUMMARY OF THE INVENTION

Accordingly the present invention provides sustained release gastro retentive swellable formulations comprising of bergenin-rich *Bergenia ciliata* extract or fraction, hydroxypropylmethylcellulose K15M, ethyl cellulose of any viscosity between 10-100 cps and sodium alginate.

In an embodiment of the invention, wherein the said bergenin-rich *Bergenia ciliata* extract or fraction comprises at least 15-40% w/w of bergenin.

In another embodiment of the invention, contains at least 20-40% w/w of bergenin-rich *Bergenia ciliata* extract or fraction, 30-40% w/w hydroxypropylmethylcellulose K15M, 15-20% w/w of ethyl cellulose (of any viscosity between 10-100 cps) and 15-20% w/w of sodium alginate.

In further embodiment of the invention the formulation is useful for the treatment of inflammatory conditions wherein proinflammatory cytokines (TNF-alpha, interleukin-6) are involved.

In yet another embodiment of the invention wherein the inflammatory disease comprise rheumatoid arthritis, cystic fibrosis, atherosclerosis and cancer.

In still another embodiment of the invention, wherein the said formulation may be in the form selected from the group consisting of a hard gelatin capsule or a tablet.

One of the feature of the invention is to provide the sustained release of bergenin in the stomach for about 16-24 hrs.

The present invention also provides a process of making sustained release gastroretentive swellable formulation comprises steps: (a) extracting dried powdered material of *Bergenia ciliate* (aerial parts) with ethanol:water (1:1) to obtain an extract solution, (b) concentrating the extract solution of step (a) by vacuum dying following up by freeze drying to obtain dry powder of hydroalcoholic extract, with an extractive value of 20-30% w/w on dry weight basis, (c) stirring the dried hydroalcoholic extract in solution of either acetone, acetonitrile or dichloromethane or as their individual mixture with hexane in the range of 50:50 to 90:10 at 50-70° C. for 4-8 hrs. to obtain soluble layer, (d) concentrating the soluble layer as obtained in step (c) by vacuum drying to obtain dry powder of bergenin rich extract with an extractive value of 5-15% w/w on dry weight basis, (e) mixing the bergenin-rich *Bergenia ciliata* extract/fraction and polymer(s) in geometric proportion for uniform distribution of the contents, (f) addition of a binder solution to the uniformly mixed powder blend to form a wet-mass, (g) passing of a wet-mass through a sieve of mesh size #10-12, (h) drying of granules in hot air at 40-70° C. for 1-2 hrs., and (i) filling of polymeric granules of *Bergenia ciliata* extract in capsules or compressed into tablet.

In another aspect of the present invention, in the comparative pharmacokinetic study conducted in SD rats, the GRSR formulation (IIIM-160-A002-SR) displayed 4-fold enhancement in the AUC of the bergenin (a bioactive constituent) in comparison to the plain extract (IIIM-160-A002).

In another embodiment of the invention, the binding agent may be selected from the group consisting of polyvinylpyrrolidone K 30, polyvinylpyrrolidone K15.

In yet another embodiment of the invention, 5-10% of binding agent may be used in isopropyl alcohol.

BRIEF DESCRIPTION OF THE DRAWINGS

FIG. 3A is an in-vitro dissolution profile of hydroalcoholic extract (BCHA) and its optimized GR-SR formulation BCHA-29. FIG. 3B is an in-vitro dissolution profile of bergenin enriched fraction (BCE-1) and its optimized GR-SR formulation BCE-8. In this study, the % release of bergenin was determined by HPLC analysis. FIG. 3C is a comparative in-vitro dissolution profile of formulations BCHA-29 and BCHA-28 of hydroalcoholic extract prepared with and without sodium alginate, respectively. FIG. 3D is a comparative in-vitro dissolution profile of formulations BCE-8 and BCE-5 of bergenin-enriched fraction prepared with and without sodium alginate, respectively.

FIG. 4A shows dimensions of capsules filled with the optimized GR-SR formulations BCHA-29, BCE-8 at zero time (before adding them in the dissolution medium) and at the end of 24 hrs. FIG. 4B shows the formula and values of swelling index at the end of 24 hrs of optimized GR-SR formulations BCHA-29, BCE-8.

FIG. 5A shows the pharmacokinetic analysis of bergenin in SD rats. FIG. 5B is a comparative oral pharmacokinetic study of plain extract (IIIM-160-A002) and GRSR formulation (IIIM-160-A002-SR) in SD rats (route of administration: PO; dose equivalent to 6.2 mg/kg of bergenin). The time-plasma concentration curve, comparison of $C_{max}$, $AUC_{last}$, $T_{max}$, $t_{1/2}$ and $T_{last}$ of plain extract and GRSR formulation are shown.

ABBREVIATIONS

Figure 1A:
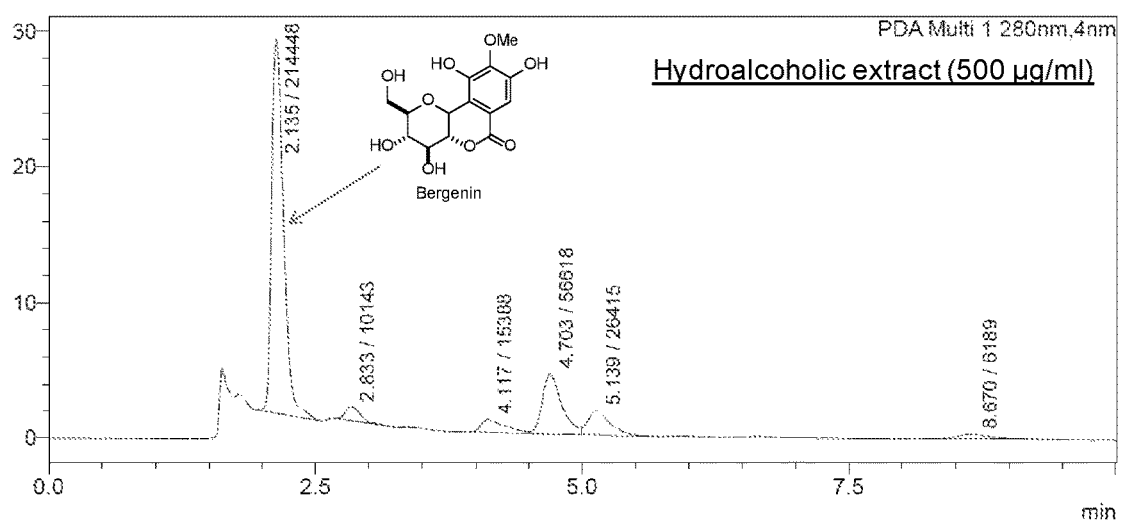
FIGS. 1A and 1B show the HPLC chromatograms of hydroalcoholic extract of *Bergenia ciliata* (FIG. 1A) and bergenin enriched fraction of *Bergenia ciliata* (FIG. 1B). Labels of each peak indicate the retention time and area under the curve. Both HPLC chromatograms are recorded at 500 µg/ml concentration.
Figure 1B:
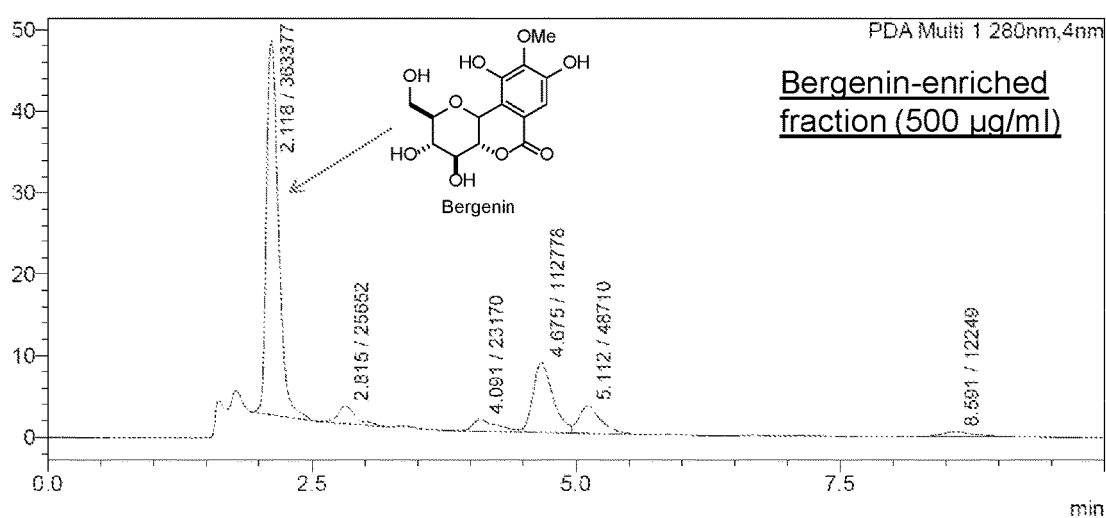

BCHA, *Bergenia ciliata* hydroalcoholic extract; BCE, *Bergenia ciliata* enriched fraction; GR-SR, gastroretentive sustained release; GRDD, gastroretentive drug delivery; GIT, gastrointestinal tract; EC, ethyl cellulose; HPLC, high performance liquid chromatography; HPMC-K15M, hydroxypropyl methyl cellulose-K15M; PVP-K30, polyvinylpyrrolidone K 30; HEC, hydroxy ethyl cellulose; TNF-alpha, tumor necrosis factor-alpha; IL-6, interleukin-6; LPS, lipopolysaccharide; PDA, photo-diode array; SGF, simulated gastric fluid; SIF, simulated intestinal fluid; SD rat, Sprague Dawley rat.

DETAILED DESCRIPTION OF THE INVENTION

The present invention provides the method for the preparation of novel drug delivery composition for the controlled release of an active ingredient in the stomach environment over a prolonged period of time. In particular, there is provided a novel gastroretentive sustained release oral formulations of *Bergenia ciliata* for supplying optimum plasma concentrations of the biologically active compound "bergenin". These novel formulations are density-controlled delivery systems, which either float or sink in gastric fluids. These dosage forms prolong the gastric retention of formulation thereby avoiding exposure of bergenin to intestinal or colonic environment where it is unstable.

The oral sustained release formulations according to one exemplary embodiment of the present invention comprises bergenin-rich extract/fraction of *Bergenia ciliata* (family: Saxifragaceae) as an active substance. The "bergenin-rich extract/fraction of *Bergenia ciliata*" is characterized for the content of bergenin ($C_{14}H_{16}O_9$, molecular weight=328.08), which should be in the range of 15-40% w/w. In this case, a mixture of water and ethanol (or water and methanol) may be used as the extraction solvent in the range of 20:80 to 80:20. The *Bergenia* extract is prepared in the form of dried lyophilized powder by extracting the aerial parts of the *Bergenia ciliata* with water and ethanol (or water and methanol) by cold maceration, filtering the extract, followed by concentrating the extract under reduced pressure. The enrichment of the extract for bergenin content, if required, can be done by further extracting the bergenin-rich fraction with acetone, acetonitrile or dichloromethane or in their mixture with hexane in the range of 50:50 to 90:10 solvent.

The novel drug release system according to one exemplary embodiment of the present invention is achieved by the use of the pharmaceutical composition comprising the bergenin-rich *Bergenia ciliata* extract/fraction mixed with an excipients i.e. expandable polymer and/or a sustained release polymer, selected from the group consisting of hydroxypropylmethylcellulose K15M, ethyl cellulose, xanthan gum, chitosan, sodium alginate. The solution of polyvinyl pyrrolidine K30 or polyvinyl pyrrolidine K90 in isopropanol, ethanol, propanol, or water was used as a binder.

In one preferred embodiment of the invention, the orally-administrable formulation for the controlled release of active ingredient 'bergenin' comprises granulated bergenin-rich *Bergenia ciliata* extract or fraction and expandable polymer/sustained release polymer in a specific ratio (extract to polymer ratio—40:60 or 20:80), and is characterized in that the total in vitro dissolution time of the formulation required for the release of 100% of the active ingredient available from the formulation, is between about 16-24 hrs, as determined by the U.S.P. dissolution apparatus by Paddle method at a speed of 50 rpm, and temperature of 37° C.±0.5, using 900 ml of dissolution media (pH 1.2 buffer).

The sustained release of the bioactive constituent "bergenin" was observed in the rat pharmacokinetic study; which validated the in-vitro dissolution results. The *Bergenia ciliata* extract (IIIM-160-A002) and its GRSR formulation, when administered orally at equivalent dose (a dose equivalent to 6.2 mg/kg of bergenin), the significantly higher AUC for "bergenin" was observed in case of GRSR formulation in comparison to the plain extract. This result indicated that GRSR formulation, controls the release of extract, leading to the release of bioactive constituent for prolonged time. As a overall effect of this, the higher amount of bergenin is available in the blood circulation (4-fold enhancement in AUC), which ultimately results in improved therapeutic effect.

In one preferred embodiment of the invention, the formulation is characterized in that it contains from 20 to 40% w/w of bergenin-rich *Bergenia ciliata* extract/fraction.

In another preferred embodiment of the invention, the formulation is in the form selected from the group consisting of a matrix tablet or a hard gelatin two-piece capsule filled with polymeric granules or microparticles of granulated extract.

The invention also comprises a process for the preparation of an orally-administrable gastroretentive formulation for the controlled release of granulated extract. The steps for preparation of said formulation comprising bergenin-rich *Bergenia ciliata* extract/fraction and polymers (namely hydroxypropyl methylcellulose K15M, ethyl cellulose (of any viscosity between 10-100 cps) and sodium alginate), comprises:

a). extraction of dried powdered material of *Bergenia ciliata* (aerial parts) with ethanol:water (1:1) to yield an extract solution b). concentrating the extract solution first by vacuum drying followed by freeze drying to yield dry powder (IIIM-160-A002). The extractive value on dry weight basis was found to be 20-30% w/w.

Further enrichment of the bergenin-content of the obtained extract was done using following steps:

c). stirring the dried hydroalcoholic extract in the solution of either acetone, acetonitrile or dichloromethane or as their individual mixture with hexane (50:50 to 90:10) at 50-70° C. for 4-8 hrs.

d). concentrating the soluble layer as obtained in step 'c' by vacuum drying to yield dry powder of bergenin-enriched fraction (IIIM-160-BEF). The extractive value of bergenin-enriched fraction from powdered plant material (on dry weight basis) was found to be 5-15% w/w.

The GR-SR formulations of the bergenin-rich *Bergenia ciliata* extract/fraction were prepared using following steps:

e). mixing the bergenin-rich *Bergenia ciliata* extract/fraction (containing at least 5% w/w of bergenin) with excipient(s) in mortor and pestle, following by addition of 10% PVP-K30 solution in isopropanol (as a binder) to form a dough.

f). passing the wet-mass through a stainless steel sieve of mesh size #10.

g). drying of granules in hot air oven at 50° C. for 30-60 min.

h). Passing the dried granules through sieve #10 and retaining on sieve #30.

i). filling the polymeric granules in two-piece hard gelatin capsules.

In another aspect of the present invention, a method for enrichment of one of the active constituent is provided.

In one more embodiment of the invention, the standardization of the bergenin-rich *Bergenia ciliata* extract/fraction is provided to identify and quantify the amount of bergenin in the standardized extract by HPLC.

In another embodiment of the invention, standardized bergenin-rich *Bergenia ciliata* extract/fraction displayed significant inhibition of proinflammatory cytokines in human monocytic THP-1 cells.

In one particular aspect of the present invention, bergenin-rich *Bergenia ciliata* extract/fraction is provided, which comprises active components for cytokine inhibition, and related manifestations and disorders with a pharmaceutically acceptable carrier, and methods of using the same. Accordingly, the present invention is directed generally to the sustained release formulations of standardized extracts or bergenin enriched fraction of *Bergenia ciliata* for treatment of inflammatory diseases wherein proinflammatory cytokines are involved.

In another aspect of the invention, inflammatory diseases comprise rheumatoid arthritis and related disorders in humans and other mammals.

Following examples are given by way of illustration and should not construe to limit the scope of invention.

EXAMPLES

Example 1

Preparation of Bergenin-Rich *Bergenia ciliata* Extract—IIIM-160-A002

The authentic plant material *Bergenia ciliata* (whole plant, aerial parts) was collected by the Biodiversity and Applied Botany Division of Indian Institute of Integrative Medicine (CSIR), Jammu, in May 2011 from Gurez Valley of the Jammu and Kashmir state of India. The plant material was taxonomically characterized and a voucher specimen (collection ID: 50902; accession number, 22413) was deposited in the Janaki Ammal Herbarium at the CSIR-IIIM, Jammu. The dried and powdered plant material (150 g) was extracted with a water/ethanol solution of 50% ethanol by volume and then freeze dried. The steps involved in the preparation of extract are as follows:

1. Mixing the aerial part of *Bergenia ciliata* with extracting hydro-alcoholic solution in the proportion of 1:1 (m/m), using ethanol as alcohol, in the initial proportion of 1 part plant ingredient to 20-30 parts of hydro-alcoholic solution, based on the mass of the materials. Performing the extraction of the compounds for a period of at least 3 hours at a room temperature in a closed reactor.

2. Filtering the mixture obtained in step 1, in order to obtain a first intermediary hydro-alcoholic extract and a first residue consisting of the components of the non-extracted plant drug.

3. Mixing the first residue consisting of the components of the non-extracted plant drug with a fresh extracting hydro-alcoholic solution, constituted of a mixture of ethanol and water in the proportion 1:1 (m/m). The mass of extracting hydro-alcoholic solution to be added is % of the mass of the first extracting hydro-alcoholic solution for a period of 3 hours at a room temperature in a closed reactor.

4. Filtering the mixture obtained in step 3, in order to obtain a second intermediary hydro-alcoholic extract and a second residue constituted of the components of the non-extracted plant drug.

5. Treating the second residue as per steps 3 and 4.

6. Evaporation of the ethanol from combined alcoholic filtrate by vacuum assisted evaporation (temperature of 40° C., vacuum of 250 mm Hg) until the mass corresponds to approximately 25% of the mass of the mixture obtained.

7. Finally, freeze-drying of the remaining extract to get free-flowing powdered extract (IIIM-160-A002; extractive value=20-30%). The % content of bergenin in IIIM-160-A002 was 5-15%.

Example 2

Preparation of Bergenin-Rich *Bergenia ciliata* Fraction—IIIM-160-BEF

1. The hydroalcoholic extract (IIIM-160-A002) as obtained above, was dissolved in either acetone, acetonitrile or dichloromethane or as their individual mixture with hexane (50:50 to 90:10) at 50-70° C. for 4-8 hrs. The ratio of extract to solvent used was 1:4 w/v. This process was repeated 3 times.

2. The combined soluble portion as obtained in above step was concentrated over vacuo rotavapor to get dried powder of active ingredient (bergenin) enriched fraction (IIIM-160-BEF). The extractive value of bergenin-enriched fraction from powdered plant material (on dry weight basis) is found to be 8% w/w. The % content of bergenin in IIIM-160-BEF was 10-25%. HPLC analysis was performed on the Shimadzu HPLC system connected to a PDA detector, and RP-8e column (Chromolith® performance, 5 μm, 100 mm×4.6 mm). Column was eluted with MeOH: 0.1% v/v Formic acid (25:75 v/v) in isocratic manner at a flow rate of 1 ml/min. The column oven temperature was 37° C. (column oven, CTO-IOASVP). The detection wavelength was 280 nm using PDA detector (SPD-M20A, Prominence, Shimadzu).

The hydroalcoholic extract IIIM-160-A002 comprises bergenin as the major component (5-15% w/w of bergenin). Enrichment of this extract using acetone, acetonitrile, dichloromethane or their individual mixture with hexane solvent resulted in enrichment up to 25-40% w/w (IIIM-160-BEF).

Example 3 pH Dependent Stability of Bergenin

Figure 2A:
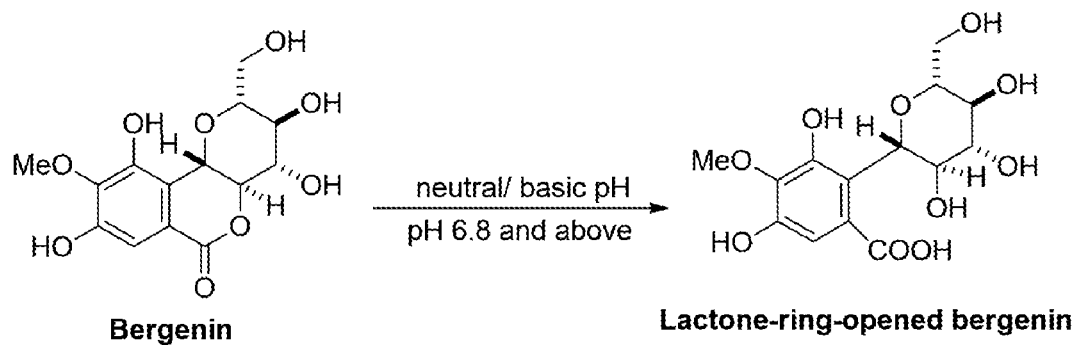
FIGS. 2A and 2B show the data for pH dependent stability of bergenin. The stability study was performed in pH 1.2 buffer, pH 4.0 buffer, phosphate buffer pH 6.8, phosphate buffered saline pH 7.4, SGF (pH 1.2), SIF (pH 6.8) and plasma. The % of bergenin hydrolyzed after 24 h was determined by HPLC analysis. Chemical reaction showing the hydrolysis of bergenin to lactone ring opened product (FIG. 2A). Graph showing the % of bergenin hydrolyzed in different media (FIG. 2B).

The stability study was performed in pH 1.2 buffer, pH 4.0 buffer, phosphate buffer pH 6.8, phosphate buffered saline pH 7.4, SGF (pH 1.2), SIF (pH 6.8) and plasma. The % of bergenin hydrolyzed after 24 h was determined by HPLC analysis. The HPLC analysis was carried out using the method as described in example 2. Results of stability studies are shown in FIGS. 2A and 2B.

Figure 2B:
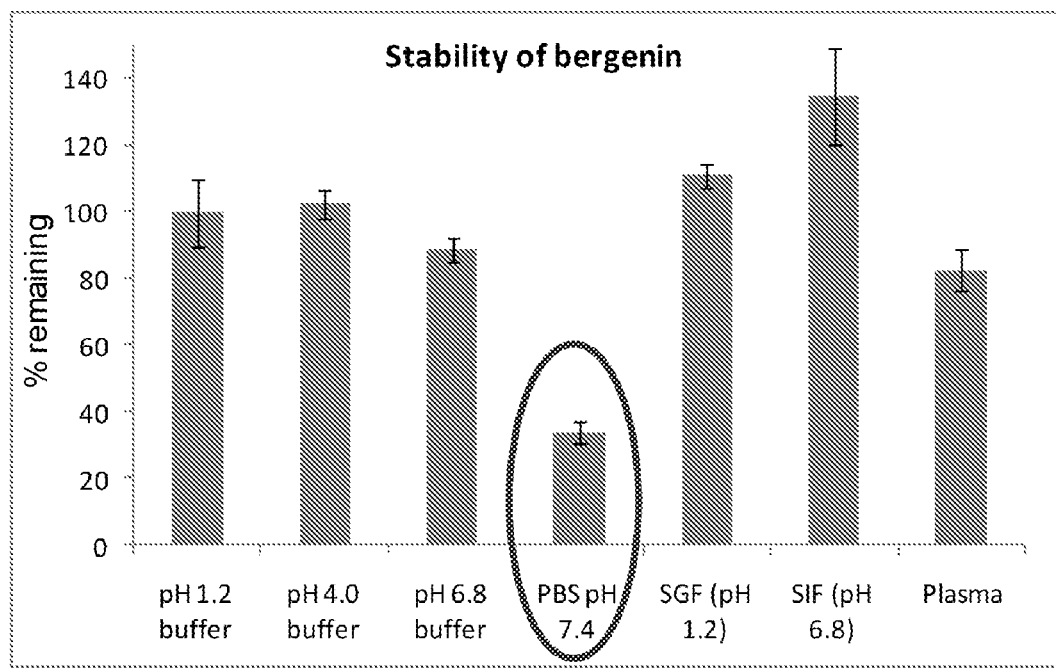

The stability results shown in FIG. 2B indicated that bergenin gets hydrolyzed to its lactone ring opened product (FIG. 2A) at pH 7.4 and above. This gives the caution that on oral administration of bergenin or bergenin-containing formulation, it should be protected from intestinal environment. These observations further support the prior report on stability concerns of bergenin.

Example 4

Preparation of Novel GR-SR Formulations

The bergenin-rich *Bergenia ciliata* extract [hydroalcoholic extract—IIIM-160-A002 or bergenin enriched fraction—IIIM-160-BEF] and excipient(s) HPMC-K15M, ethyl cellulose (of any viscosity between 10-100 cps) and sodium alginate were weighed accurately in the ratio of 40:30:15:15 or 20:40:20:20 and mixed thoroughly using mortar and pestle. This mixture was kneaded using 10% PVP-K30 solution in isopropanol (as a binder) to form a dough. This dough was then passed through sieve #10. The obtained granules were dried in oven at 50° C. for 30-60 min. The dried granules were passed through sieve #10 and retained on sieve #30. The dried granules were stored in air-tight container in vacuum desiccator till further analysis. The formulations were assayed for bergenin content using HPLC method as mentioned in example 2. Based on the results of assay, formulation equivalent to 50 mg of bergenin was filled into the hard gelatin capsules of size '0'. These capsules were analyzed for in-vitro dissolution profile. The composition and % release of bergenin of GR-SR formulations are provided in Table 1.

TABLE 1

Composition of each formulation, % release of bergenin during dissolution study and swelling, floating, intactness of formulations

| Sr No | Formulation code | Composition of the formulation[a] | Swellable (at the end of 24 h) | Sink/float (at the end of 24 h) | Intact matrix form after 24 h | % release of bergenin after | | |
|---|---|---|---|---|---|---|---|---|
| | | | | | | 0.5 h | 16 h | 24 h |
| 1 | BCHA-14R | IIIM-160-A002: 2 g<br>HPMC-K15M: 1.333 g | Yes | Float-dispersed | No | 32 | 100 | 100 |
| 2 | BCHA-18R | IIIM-160-A002: 2 g<br>HPMC-K15M: 0.888 g<br>Ethyl cellulose 10 cps: 0.444 g | Yes | Float | Yes | 38 | 100 | 100 |
| 3 | BCHA-20 | IIIM-160-A002: 2 g<br>HPMC-K15M: 0.1066 g<br>Ethyl cellulose 10 cps: 0.266 g | Yes | Float | Yes | 46 | 100 | 100 |
| 4 | BCHA-22 | IIIM-160-A002: 2 g<br>HPMC-K3OM: 1.333 g | Yes | Float-dispersed | No | 40 | 97 | 100 |
| 5 | BCHA-23 | IIIM-160-A002: 2 g<br>HPMC-K100M: 1.333 g | Yes | Float-dispersed | No | 38 | 100 | 100 |
| 6 | BCHA-28 | IIIM-160-A002: 2 g<br>HPMC-K15M: 1.333 g<br>Ethyl cellulose 10 cps: 0.666 g | Yes | Float | Yes | 26 | 96 | 100 |
| 7 | BCHA-29 | IIIM-160-A002: 2 g<br>HPMC-K15M: 1.5 g<br>Ethyl cellulose 10 cps: 0.75 g<br>Sodium alginate: 0.75 g | Yes | Float | Yes | 25 | 93 | 100 |
| 8 | BCE-5 | IIIM-160-BEF: 2 g<br>HPMC-K15M: 3.111 g<br>Ethyl cellulose 10 cps: 1.555 g | Yes | Sink | Yes | 34 | 95 | 99 |
| 9 | BCE-8 | IIIM-160-BEF: 0.5 g<br>HPMC-K15M: 1.0 g<br>Ethyl cellulose 10 cps: 0.5 g<br>Sodium alginate: 0.5 g | Yes | Sink | Yes | 21 | 94 | 100 |
| 10 | BCHA (plain hydro-alcoholic extract filled in capsules) | IIIM-160-A002 (extract equivalent of 50 mg of bergenin was filled in capsules) | No | Dispersed into the dissolution medium | No | 100 | — | — |
| 11 | BCE-1 (plain bergenin enriched fraction filled in capsules) | IIIM-160-BEF (enriched fraction equivalent of 50 mg of bergenin was filled in capsules) | No | Dispersed into the dissolution medium | No | 100 | — | — |

[a]10% PVP-K30 solution in isopropanol was added as a binder in each formulation to form a dough.

Example 5

Dissolution Profile of GR-SR Formulations

The dissolution profile of capsules filled with bergenin-rich *Bergenia ciliata* extract/fraction and their GR-SR formulations was studied using USP dissolution apparatus as per the protocol given in USP 2011 (The United States Pharmacopoeial Convention. 2011, Pages 1-8). Lab-India Dissolution Tester (Model: DS 8000; apparatus 2—Paddle Apparatus) was used for this study. Various parameters are: RPM=50; Temp.=37° C. 0.5; Volume of dissolution medium=900 ml; Dissolution medium=Hydrochloric acid buffer (pH 1.2) for 24 h, sampling time points (h)=0.5, 1, 2, 4, 8, 12, 16, 20 and 24.

The percent release of bergenin from formulations was determined by HPLC analysis. Results showed that bergenin gets 100% released in 30 min in case of capsules filled with plain hydroalcoholic extract (BCHA) as well as in bergenin enriched fraction (BCE-1). However, capsules filled with novel GR-SR formulations BCHA-18R, BCHA-28, BCHA-29, BCE-5, and BCE-8 resulted in a delayed release of bergenin with 100% release up to 24 hrs. The composition of representative formulation batches are given in Table 1. The optimized GR-SR formulation BCHA-29 comprises the use of HPMC-K15M, ethyl cellulose 10 cps and sodium alginate in the ratio of 2:1:1. The overall drug:polymer ratio in this formulation is 40:60% w/w.

Figure 3A:
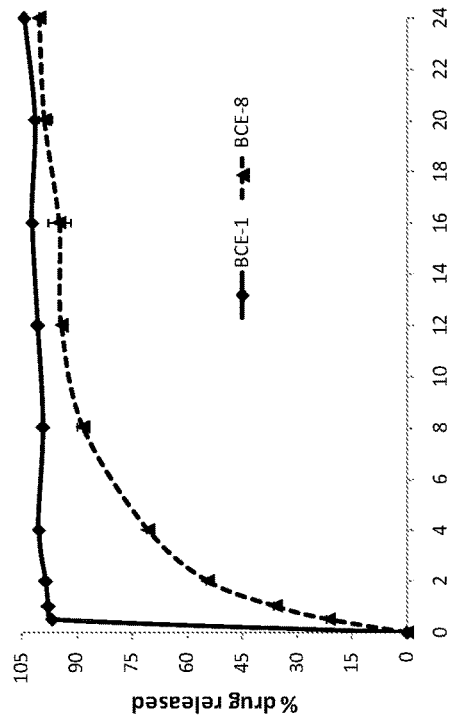
FIGS. 3A-3D show the in-vitro dissolution profiles of developed gastroretentive sustained release formulations.
Figures 4A, 4B:
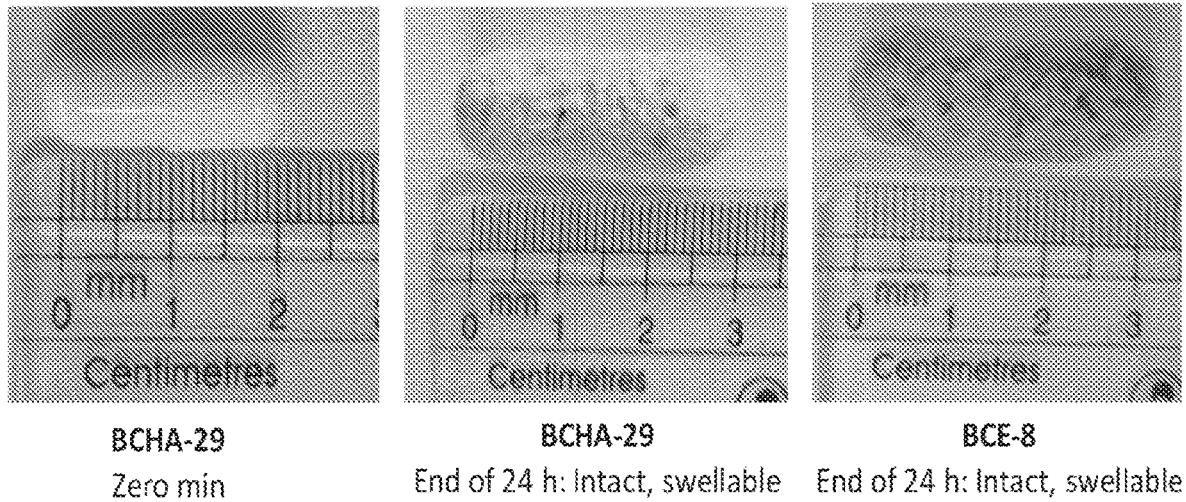
FIGS. 4A and 4B include photographs of GR-SR formulations recorded during in-vitro dissolution experiment.

The dissolution profiles of optimized GR-SR formulation BCHA-29 of hydroalcoholic extract of Bergenia ciliata is shown in FIG. 3A. The BCHA-29 was considered as the optimum batch with gastroretentive and sustained release profile over a period of 24 h. The plain hydroalcoholic extract (BCHA) showed 100% release of bergenin in 30 min, whereas the GRSR formulation BCHA-29 showed only 25% release of bergenin after 30 min. BCHA-29 was swellable (swelling index of 361%; results are shown in FIG. 4B) and also floated in intact form till 24 hrs. The photographs of BCHA-29 formulation before and after dissolution study are shown in FIG. 4A.

Figure 3B:
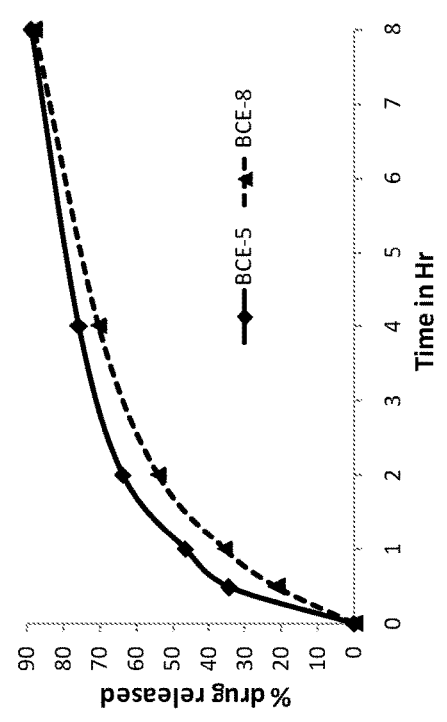

Similarly, amongst various combination of polymer to IIIM-160-BEF (bergenin enriched fraction) attempted, the optimized GR-SR formulations BCE-5, and BCE-8 resulted in a delayed release of bergenin with 100% release up to 24 hrs (FIG. 3B). The % release of bergenin after 0.5, 16 and 24 hrs is given in Table 1. The plain bergenin enriched fraction (BCE-1) showed 100% release of bergenin in 30 min, whereas the GRSR formulations BCE-5 and BCE-8 showed only 34 and 21% release of bergenin after 30 min, respectively. The optimized GR-SR formulation BCE-8 of bergenin enriched fraction comprises the use of polymers HPMC-K15M, ethyl cellulose 10 cps and sodium alginate in the ratio of 2:1:1. The overall drug:polymer ratio in this formulation is 20:80% w/w.

Figure 3C:
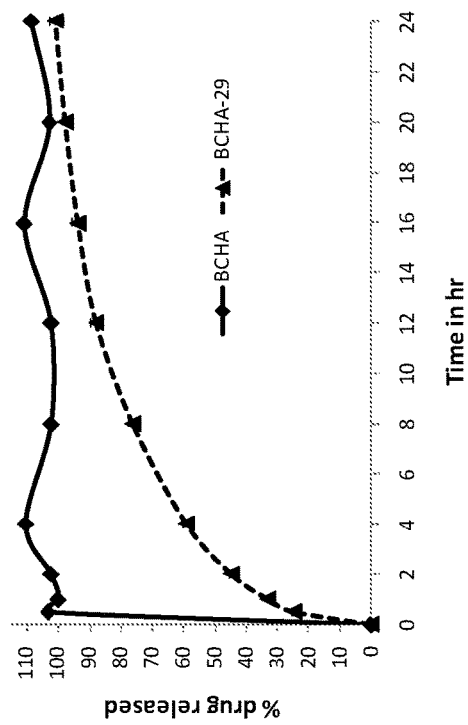
Figure 3D:
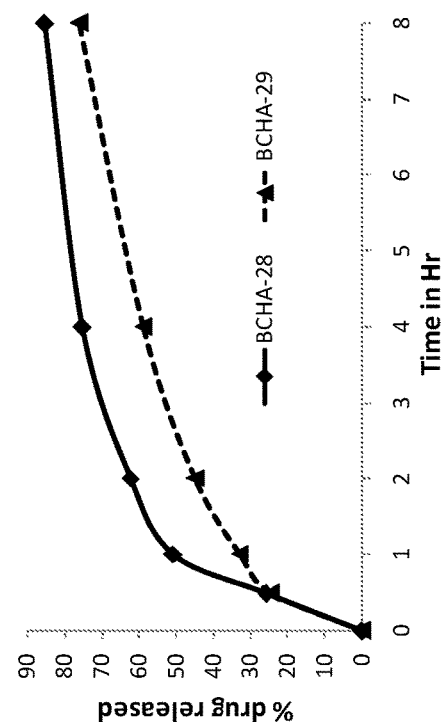

The comparative profile of GR-SR formulations of hydroalcoholic extract and bergenin-enriched fraction, with and without sodium alginate has been shown in FIGS. 3C and 3D. The formulation BCHA-28 (comprising HPMC K15M and ethyl cellulose 10 cps) showed 51, 62 and 75% release of the bergenin after 1, 2 and 4 hrs, respectively. However, the sodium alginate containing formulation BCHA-29 (comprising HPMC K15M, ethyl cellulose 10 cps and sodium alginate) showed 33, 45 and 59% release of the bergenin after 1, 2 and 4 hrs, respectively. Similar dissolution profile was observed in case of formulations containing bergenin-enriched fraction. The formulation BCE-5 (comprising HPMC K15M and ethyl cellulose 10 cps) showed 46, 63 and 75% release of the bergenin after 1, 2 and 4 hrs, respectively. However, the sodium alginate containing formulation BCE-8 (comprising HPMC K15M, ethyl cellulose 10 cps and sodium alginate) showed 35, 54 and 70% release of the bergenin after 1, 2 and 4 hrs, respectively. These results indicate that the initial burst release has been significantly reduced by incorporation of sodium alginate into the formulations.

The summarized overview of optimized formulations with their $T_{10\%}$, $T_{50\%}$ and $T_{75\%}$ values are shown in Table 2. The release half-life (Tso %) for bergenin in plain extract and bergenin-enriched fraction is less than 0.5 hr, whereas it is 4 hrs and 2 hrs in GR-SR formulations BCHA-29 and BCE-8. The $T_{75\%}$ (time taken to release 75% of drug from the formulation) for bergenin in plain extract and fraction is less than 0.5 hr, whereas it is 8 and 5 hrs in GR-SR formulations BCHA-29 and BCE-8.

TABLE 2

Dissolution release profile of bergenin in optimized formulations of Bergenia ciliata

| Formulation | Formulation batch no. | $t_{10\%}$ (hr) | $t_{50\%}$ (hr) | $t_{75\%}$ (hr) |
|---|---|---|---|---|
| Formulations of hydroalcoholic extract | BCHA (plain hydroalcoholic extract) [IIIM-160-A002] | — | — | <0.5 |
| | BCHA-29 | <0.5 | ~4.0 | ~8.0 |
| Formulations of bergenin-enriched fraction | BCE-1 (plain bergenin enriched fraction) [IIIM-160-BEF] | — | — | <0.5 |
| | BCE-8 | <0.5 | ~2.0 | ~5.0 |

$t_{10\%}$ = time taken to release 10% of drug from the formulation; $t_{50\%}$ = dissolution half-life; $t_{75\%}$ = time taken to release 75% of drug from the formulation.

Example 6

Calculating the Swelling Index of Optimized GR-SR Formulations

The swelling index of optimized GR-SR formulations during USP dissolution study was calculated using the formula as shown in FIG. 4B. The weight and dimensions of the capsule at zero time and at the end of dissolution study (i.e. after 24 hrs) were noted. After 24 hrs, the swollen capsules were removed from the solution, immediately wiped with a paper towel to remove surface droplets, and weighed.

The floating ability (float or sink) was also determined by visual observation. The floating time was defined as the time when the capsule floated on the top surface of 900 mL of the dissolution medium at 37.0 t 0.5° C.

As shown in the FIG. 4A, the dimensions of the GR-SR formulations were increased from 2 cm to 3 cm because of the swelling. The swelling index calculated based on the weights noted at 'zero' and 24 hr time, indicated that GR-SR formulations BCHA-18, BCHA-28, BCHA-29 and BCE-8 showed >358% swelling index, which results in the buoyancy (float or sink) to the formulation. This phenomenon has resulted in retaining of these formulations in the stomach and does not allow it to reach intestine.

Example 7

Pharmacokinetic Study of Bergenin, IIIM-160-A002 Extract (BCHA) and GRSR Formulation The study was performed in male SD rats. To determine oral bioavailability of bergenin, the bergenin was administered at 5 mg/kg by IV route and at 50 mg/kg by oral route. For comparative oral pharmacokinetic study of plain extract (IIIM-160-A002) and GRSR formulation (filled in 9el capsules), the dose equivalent to 6.2 mg/kg of bergenin was administered in SD rats in both these groups. Blood samples were collected (n=3/time point) at 0.083 (IV only), 0.25, 0.5, 1, 2, 4, 8 and 24 h, post-dose. At each time point about 200 µL of blood was collected by jugular vein into a labeled microfuge tube containing 200 mM K2EDTA solution (20 µL per mL of blood) and equivalent volume of heparinized saline was replaced following sample collection. The blood samples were processed to obtain the plasma samples within 30 min of scheduled sampling time. All plasma samples were stored below −60° C. until bioanalysis. The plasma samples were analyzed for bergenin content using a fit-for purpose LC-MS/MS method with a lower limit of quantification (LLOQ) of 9.95 ng/mL. The pharmacokinetic parameters of bergenin were calculated using the non-compartmental analysis tool of validated Phoenix® WinNonlin® software (version 6.3).

Figure 5A:
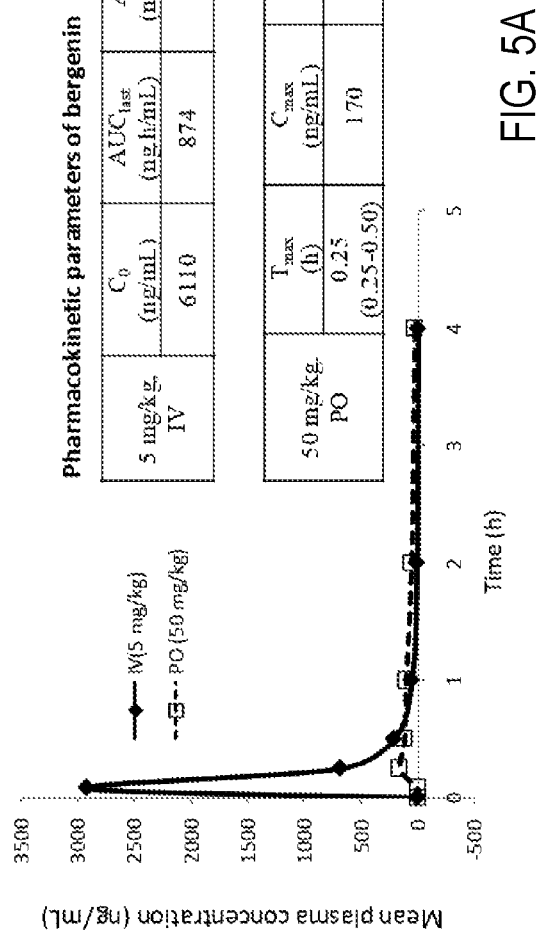
FIGS. 5A and 5B show pharmacokinetic studies of bergenin, plain extract (IIIM-160-A002) and GRSR formulation (IIIM-160-A002-SR) in SD rats.

Following a single intravenous bolus administration of "bergenin" to male SD rats (5 mg/kg), the mean plasma clearance (Cl) was found to be high (95.5 mL/min/kg which is almost 1.74-folds higher than the normal hepatic blood flow of 55 mL/min/kg in rats) with elimination half-life ($t_{1/2}$) of 0.318 h. The volume of distribution at steady state was found to be 1.05 L/kg which is almost 1.50-fold higher than the normal total body water content (0.7 L/kg in rats). Mean plasma exposure ($AUC_{last}$) was found to be 874 h*ng/mL. Following a single oral gavage administration of "bergenin" to male SD rats (50 mg/kg), median time to reach the maximum plasma concentration was found to be 0.25 h with peak plasma concentration ($C_{max}$) of 170 ng/mL. Plasma exposure ($AUC_{last}$) was found to be 269 h*ng/mL. The terminal plasma half-life was found to be 1.74 h. The absolute oral bioavailability of bergenin was determined to be 3% (FIG. 5A).

Figure 5B:
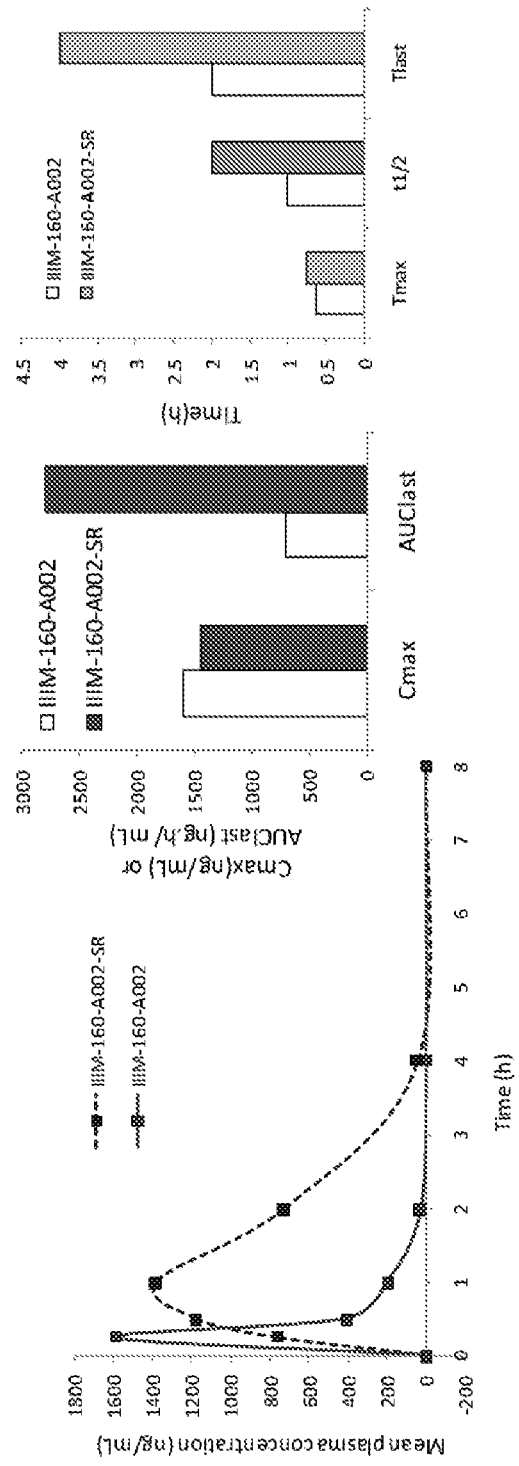
Figure 6:
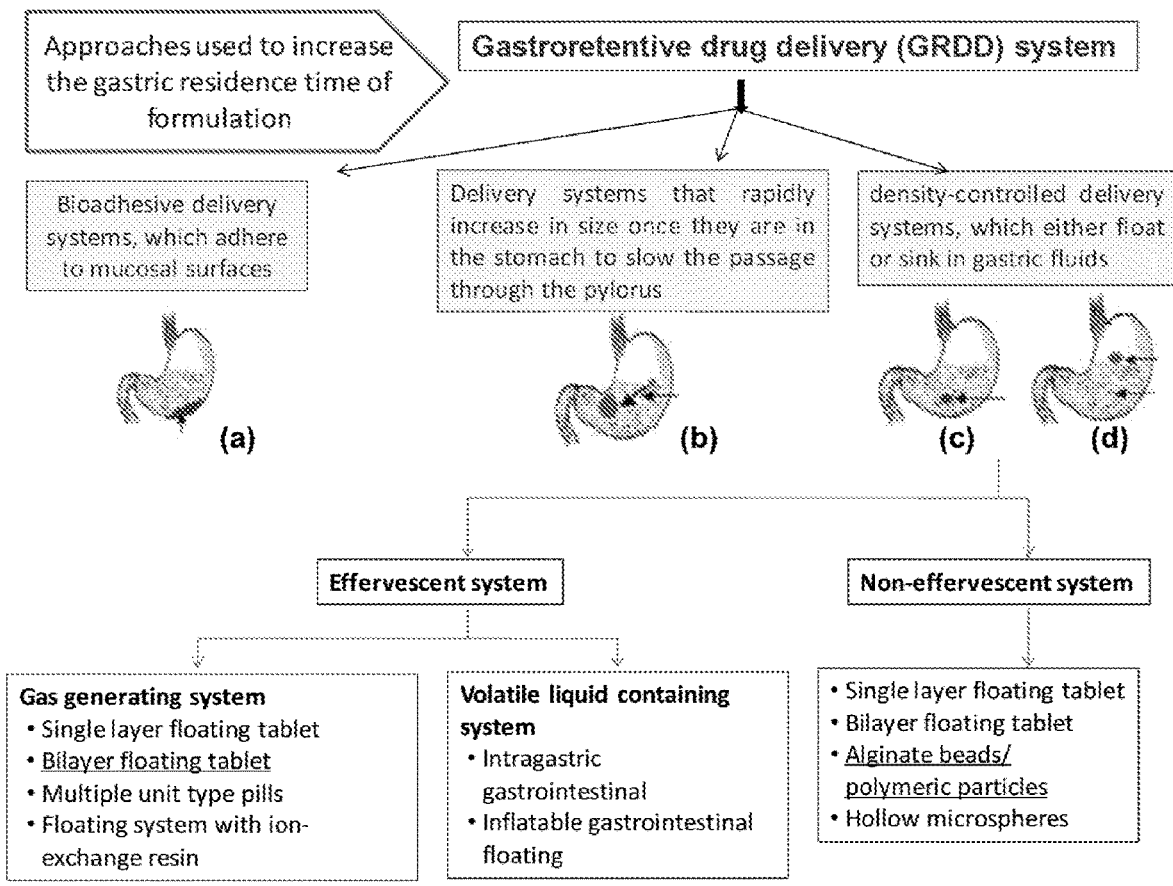
FIG. 6 is a pictorial representation of floating drug delivery systems.

The comparative oral pharmacokinetic analysis of plain hydroalcoholic extract and GRSR formulation was performed in SD rats. The extract/formulation equivalent to 6.2 mg/kg of bergenin were filled in the 9el capsules, which were delivered to rats by oral route. The PK results indicated that there is 4-fold increase in the $AUC_{last}$ of bergenin in case of GRSR formulation in comparison to that of plain extract. Similarly, the $T_{max}$, $t_{1/2}$ and $T_{last}$ values were increased in GRSR formulation in comparison to plain extract, because of the sustained release of the bergenin in formulations. The time-plasma concentration curve of extract and formulation is depicted in FIG. 5B.

Example 8

In-Vitro Cytokine Inhibition in THP-1 Cells

For the in vitro analysis of pro-inflammatory cytokines (IL-6 and TNF-α), human leukemia THP-1 cells were seeded in a 24-well plate at a density of 4×10$^5$ cells/ml of RPMI medium per well. THP-1 cells were then treated with phorbol 12-myristate 13-acetate (20 ng/ml) for differentiation into macrophages for 18 h followed by a rest period of 48 h. Cells were further co-treated with test samples and 1 μg/ml of lipopolysaccharide (LPS) in a serum-free medium. Culture supernatant was harvested after 24 h for analysis of different cytokines by using OptEIA ELISA Kits from BD Biosciences. Total protein content for all the samples was calculated by using Bradford reagent from Bio-Rad Laboratories. All the samples were normalized by dividing cytokine concentration with total quantity of protein. Results are shown in Table 3. Bergenin was reported earlier as an inhibitor of TNF-alpha and IL-6 and was therefore was used as a positive control in this assay.

The LPS induced release of TNF-alpha and IL-6 was significantly suppressed by hydroalcoholic extract/fraction at the test concentration of 12 μg/ml. The significantly better inhibition profile of bergenin enriched fraction was observed.

TABLE 3

Cytokine inhibition results of hydroalcoholic extract, bergenin-enriched fraction and bergenin in THP-1 cells

| | Inhibition of TNF-α and IL-6 by hydroalcoholic extract, bergenin-enriched fraction and bergenin in THP-1 cells | | | |
|---|---|---|---|---|
| Sample | TNF-α (pg/mL)/ total protein (μg) | % inhibition of TNF-α | IL-6 (pg/mL)/ total protein (μg) | % inhibition of IL-6 |
| Control | 0.560 ± 0.130 | 0 | −0.714 ± 0.104 | 0 |
| LPS | 6.016 ± 0.131 | 0 | 10.34 ± 0.204 | 0 |
| IIIM-160-A002 (12.5 μg/mL) | 2.43 ± 0.28 | 60 | −0.588 ± 0.317 | 100 |
| IIIM-160-BEF (12.5 μg/mL) | 1.74 ± 0.28 | 71 | −0.646 ± 0.757 | 100 |
| Bergenin (12.5 μg/mL) | 2.40 ± 0.25 | 61 | 0.08 ± 0.107 | 98 |

ADVANTAGES OF THE INVENTION

The main advantages of the present invention are:
The novel formulations provide prolonged retention of the active ingredients in stomach, and therefore avoid its intestinal degradation.
Novel formulations provides sustained release of active ingredients in stomach for about 16-24 hrs.
An improvement in therapeutic effectiveness.
Reduction in drug loss.
The novel formulations provide prolonged and steady plasma concentrations of bergenin over 24 hours and thus it can help in avoiding under-dosing between dosage intervals.
The novel formulations are free-flowing and non-hygroscopic.
The excipients/polymers used in the formulations are within the acceptable limits.
Bergenin-rich *Bergenia ciliata* extract is capable of strongly inhibiting proinflammatory cytokines TNF-alpha and IL-6.

We claim:

1. A tablet or capsule for treating an inflammatory disease involving pro-inflammatory cytokines TNF-alpha or interleukin-6 in a human in need thereof, the tablet or capsule consisting of therapeutically effective amounts of a hydroalcoholic extract of *Bergenia ciliata*, polyvinylpyrrolidone, and hydroxypropylmethylcellulose.

2. The tablet or capsule of claim 1, wherein the inflammatory disease is selected from the group consisting of rheumatoid arthritis, cystic fibrosis, and atherosclerosis.

3. The tablet or capsule of claim 1, wherein the weight ratio of the hydroalcoholic extract of *Bergenia ciliata* to the hydroxypropylcellulose is 20:80 or 40:60.

4. The tablet or capsule of claim 1, wherein the hydroalcoholic extract of *Bergenia ciliata* has a bergenin content of at least 5% w/w.

5. The tablet or capsule of claim 4, wherein the tablet or capsule displays a sustained release of the bergenin of up to 24 hours in the stomach of the human in need thereof.

6. The tablet or capsule of claim 1, which is a hard gelatin capsule or a tablet.

7. The tablet or capsule of claim 4, wherein the hydroalcoholic extract of *Bergenia ciliata* is prepared by a process consisting of:

(a) extracting dried powdered aerial parts of *Bergenia ciliata* with an ethanol:water mixture at a ratio of 1:1 to obtain an extract solution;
(b) concentrating the extract solution of (a) by vacuum drying the extract solution, followed by freeze drying the vacuum dried extract solution, to obtain a dry powder of hydroalcoholic extract;
(c) stirring the dried powder of hydroalcoholic extract in a solution with a solvent selected from the group consisting of acetone, acetonitrile, dichloromethane, and hexane in the range of 50:50 to 90:10 extract to solvent, respectively, at a temperature from 50° C. to 70° C. for 4 hours to 8 hours to obtain a soluble layer; and
(d) concentrating the soluble layer obtained in (c) by vacuum drying the soluble layer to obtain the tablet or capsule of claim 1.

\* \* \* \* \*